US011253648B2

(12) United States Patent
Tennican et al.

(10) Patent No.: US 11,253,648 B2
(45) Date of Patent: Feb. 22, 2022

(54) MULTI-CHAMBER INJECTION DEVICE

(71) Applicant: Hyprotek, Inc., Spokane, WA (US)

(72) Inventors: Patrick O. Tennican, Spokane, WA (US); L. Myles Phipps, Shelton, WA (US)

(73) Assignee: Hyprotek, Inc., Spokane, WA (US)

( * ) Notice: Subject to any disclaimer, the term of this patent is extended or adjusted under 35 U.S.C. 154(b) by 94 days.

(21) Appl. No.: 14/776,657

(22) PCT Filed: Mar. 14, 2014

(86) PCT No.: PCT/US2014/028820
§ 371 (c)(1),
(2) Date: Sep. 14, 2015

(87) PCT Pub. No.: WO2014/144416
PCT Pub. Date: Sep. 18, 2014

(65) Prior Publication Data
US 2016/0030671 A1 Feb. 4, 2016

Related U.S. Application Data

(60) Provisional application No. 61/801,275, filed on Mar. 15, 2013.

(51) Int. Cl.
*A61M 5/19* (2006.01)
*A61M 5/00* (2006.01)
(Continued)

(52) U.S. Cl.
CPC ............. *A61M 5/19* (2013.01); *A61M 5/001* (2013.01); *A61M 5/008* (2013.01); *A61M 5/284* (2013.01);
(Continued)

(58) Field of Classification Search
CPC ...... A61M 5/19; A61M 5/008; A61M 39/223; A61M 2005/1787; A61M 39/22;
(Continued)

(56) References Cited

U.S. PATENT DOCUMENTS 3,107,785 A * 10/1963 Rochr ................. A61M 5/3205
206/365
4,367,737 A * 1/1983 Kozam .................. A61M 5/19
604/191
(Continued)

FOREIGN PATENT DOCUMENTS

CN 2568155 Y 8/2003
CN 101854969 A 10/2010
(Continued)

OTHER PUBLICATIONS

The Extended European Search Report dated Nov. 16, 2016 for European patent application No. 14762874.7, 6 pages.
(Continued)

*Primary Examiner* — Brandy S Lee
*Assistant Examiner* — Hong-Van N Trinh
(74) *Attorney, Agent, or Firm* — Lee & Hayes PC; Thu Nguyen

(57) ABSTRACT

A multi-chamber injection device includes multiple syringes. The multiple syringes may be arrayed in a circular, linear, or other format. In some implementations, a needle, port, or similar may be shared by all the syringes in configuration that allows only one syringe to deliver contents at a time while blocking the other syringes from delivering their respective contents. In some implementations, the syringes may be all stored in the same container. One or more of the chambers of a multi-chamber injection device may be preloaded with medication. Different medi-
(Continued)

cations may be loaded into different chambers. The medications may be selected to treat the same medical condition.

12 Claims, 8 Drawing Sheets

(51) Int. Cl.
    *A61M 5/32*         (2006.01)
    *A61M 5/315*       (2006.01)
    *A61M 39/22*       (2006.01)
    *A61M 5/28*         (2006.01)
    *A61M 5/178*       (2006.01)
    *A61M 5/34*         (2006.01)
    *A61M 5/31*         (2006.01)

(52) U.S. Cl.
    CPC .... *A61M 5/31511* (2013.01); *A61M 5/31515* (2013.01); *A61M 5/32* (2013.01); *A61M 5/3202* (2013.01); *A61M 5/3213* (2013.01); *A61M 39/223* (2013.01); *A61M 2005/1787* (2013.01); *A61M 2005/3109* (2013.01); *A61M 2005/3128* (2013.01); *A61M 2005/31508* (2013.01); *A61M 2005/31518* (2013.01); *A61M 2005/341* (2013.01); *A61M 2205/6063* (2013.01); *A61M 2205/6081* (2013.01)

(58) Field of Classification Search
    CPC ............ A61M 5/16827; A61M 5/3295; A61M 2005/3104; A61M 5/3202; A61M 2005/004; A61M 5/3213; A61M 2005/3109; A61M 5/002; A61M 5/3205; A61M 2005/3107; A61M 5/3298; A61M 5/32; A61M 2005/005; A61M 5/31; A61M 2005/3103; A61M 5/284; A61M 5/31511; A61M 5/31515; A61M 2005/3128; A61M 2005/31508; A61M 5/31518; A61M 2005/341; A61M 2205/6063; A61M 2205/6081; A61M 5/2066; A61M 5/00; A61M 5/28; A61M 5/178; A61M 5/1407; A61M 5/1408; A61M 5/24; A61M 5/001; A61B 50/30; A61B 50/3001; A61B 50/362
    See application file for complete search history.

(56) References Cited

U.S. PATENT DOCUMENTS

| | | | | |
|---|---|---|---|---|
| 4,446,970 | A | | 5/1984 | Further |
| 4,657,138 | A | | 4/1987 | Watson |
| 4,758,235 | A | * | 7/1988 | Tu ....................... A61M 39/223 251/311 |
| 5,190,521 | A | * | 3/1993 | Hubbard ............... A61M 5/422 604/117 |
| 5,411,485 | A | * | 5/1995 | Tennican ............ A61M 5/1408 600/432 |
| 5,665,066 | A | | 9/1997 | Fischer |
| 5,928,215 | A | * | 7/1999 | Caizza ................ A61M 5/3202 604/411 |
| 6,979,316 | B1 | * | 12/2005 | Rubin .................... A61M 5/326 604/156 |
| 7,416,540 | B2 | * | 8/2008 | Edwards ............. A61M 5/2033 604/144 |
| 9,427,514 | B2 | * | 8/2016 | Bruehwiler ......... A61M 5/3205 |
| 2003/0040701 | A1 | * | 2/2003 | Dalmose ........... A61M 5/31596 604/87 |
| 2004/0084047 | A1 | * | 5/2004 | Hickle ............... A61M 16/0084 128/203.13 |
| 2006/0079846 | A1 | | 4/2006 | Williams |
| 2006/0118199 | A1 | | 6/2006 | Yamazaki |
| 2008/0142554 | A1 | | 6/2008 | Lafferty |
| 2008/0154213 | A1 | * | 6/2008 | Kiehne ............. A61M 5/31501 604/220 |
| 2008/0255520 | A1 | | 10/2008 | Henderson |
| 2012/0197208 | A1 | * | 8/2012 | Bruggemann ........ A61M 5/002 604/192 |

FOREIGN PATENT DOCUMENTS

| | | |
|---|---|---|
| JP | 2004500906 | 1/2004 |
| JP | 2004321579 | 11/2004 |
| JP | 2008511349 A | 4/2008 |
| JP | 2008528210 | 7/2008 |
| JP | 2011005280 | 1/2011 |
| JP | 2012531382 | 12/2012 |
| WO | WO2005018830 | 3/2005 |
| WO | WO2006024172 A1 | 3/2006 |
| WO | WO2007003063 | 1/2007 |
| WO | WO2009016161 | 2/2009 |
| WO | WO2012043194 | 4/2012 |
| WO | WO2012121691 | 9/2012 |

OTHER PUBLICATIONS

Translated Chinese Office Action dated May 31, 2017 for Chinese patent application No. 201480012814.5, a counterpart foreign application of U.S. Appl. No. 14/776,657, 11 pages.
The PCT Search Report and Written Opinion dated Aug. 27, 2014 for PCT application No. PCT/US14/28820, pages.
The Australian Office Action dated Aug. 13, 2018 for Australian Application No. 2014229072, a counterpart foreign application of U.S. Appl. No. 14/776,657, 5 pages.
Translated Russian Office Action dated Jun. 7, 2018 for Russian patent application No. 2015144180, a counterpart foreign application of U.S. Appl. No. 14/776,657, 12 pages.
Translated Chinese Office Action dated Feb. 26, 2018 for Chinese patent application No. 201480012814.5, a counterpart foreign application of U.S. Appl. No. 14/776,657, 23 pages.
Translated Japanese Office Action dated Jan. 23, 2018 for Japanese Patent Application No. 2016-502910, a counterpart foreign application of U.S. Appl. No. 14/776,657, 13 pages.
Translated Russian Office Action dated Feb. 12, 2018 for Russian patent application No. 2015144180, a counterpart foreign application of U.S. Appl. No. 14/776,657, 11 pages.
Translated Chinese Office Action dated Sep. 27, 2018 for Chinese patent application No. 201480012814.5, a counterpart foreign application of U.S. Appl. No. 14/776,657, 18 pages.
The European Office Action dated Oct. 25, 2018 for European patent application No. 14762874.7, a counterpart foreign application fo U.S. Appl. No. 14/776,657, 4 pages.
The Russian Office Action, dated Oct. 19, 2018, for Russian Patent Application No. 2015144180, a counterpart foreign application of the U.S. Appl. No. 14/776,657, 13 pages.
Translated Japanese Office Action dated Sep. 17, 2019 for Japanese Patent Application No. 2018-195236, a counterpart foreign application of U.S. Appl. No. 14/776,657, 6 pages.
The Brazilian Office Action dated Jan. 3, 2020 for Brazilian Patent Application No. BR112015023007-5, a counterpart foreign application of U.S. Appl. No. 14/776,657, 7 pages.
The Canadian Office Action dated Feb. 5, 2020 for Canadian Patent Application No. 2,903,832, a counterpart foreign application of U.S. Appl. No. 14/776,657, 4 pages.
The European Office Action dated Feb. 11, 2020, for European Patent Application No. 14762874.7, a counterpart foreign application of U.S. Appl. No. 14/776,657, 5 pages.
The Indian Office Action dated Aug. 18, 2020 for Indian Patent Application No. 7875/DELNP/2015, a counterpart of U.S. Appl. No. 14/776,657, 6 pages.
The Brazilian Office Action dated Aug. 31, 2021 for Brazilian Patent Application No. BR112015023007-5, a counterpart of U.S. Appl. No. 14/776,657, 8 pages.

(56) References Cited

OTHER PUBLICATIONS

Canadian Office Action dated Apr. 6, 2021 for Canadian Patent Application No. 2,903,832, a counterpart foreign application of U.S. Appl. No. 14/776,657, 3 pages.
Korean Office Action dated Nov. 12, 2020 for Korean Patent Application No. 10-2015-7024319, a counterpart foreign application of U.S. Appl. No. 14/776,657, 17 pages.

* cited by examiner

MULTI-CHAMBER INJECTION DEVICE

CROSS-REFERENCE TO RELATED APPLICATION

This Application claims priority to and is a national phase of PCT Patent Application No. PCT/US2014/028820, filed on Mar. 14, 2014, which claims priority to and the benefit of U.S. Provisional Patent Application No. 61/801,275, filed on Mar. 15, 2013, and entitled "Multi-Chamber Injection Device." PCT Patent Application No. PCT/US2014/028820 and U.S. Provisional Patent Application No. 61/801,275 are hereby incorporated by reference in their entirety.

BACKGROUND

Drug injection is an effective technique for delivering medication directly to the bloodstream of a patient. However, conventional syringes and other injection devices may be difficult to use and inconvenient to use for drug delivery particularly when emergent medical conditions benefit from rapid treatment. Accordingly, there is a need for improved injection devices.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

A multi-chamber injection device includes multiple syringes. The multiple syringes may be arrayed in a circular, linear, or other format. In some implementations, a needle, port, or similar may be shared by all the syringes in a configuration that allows only one syringe to deliver contents at a time while blocking the other syringes from delivering their respective contents. One or more of the chambers of a multi-chamber injection device may be preloaded with medication. Different medications may be loaded into different chambers. The medications may be selected to treat the same medical condition.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figures 1A, 1B:
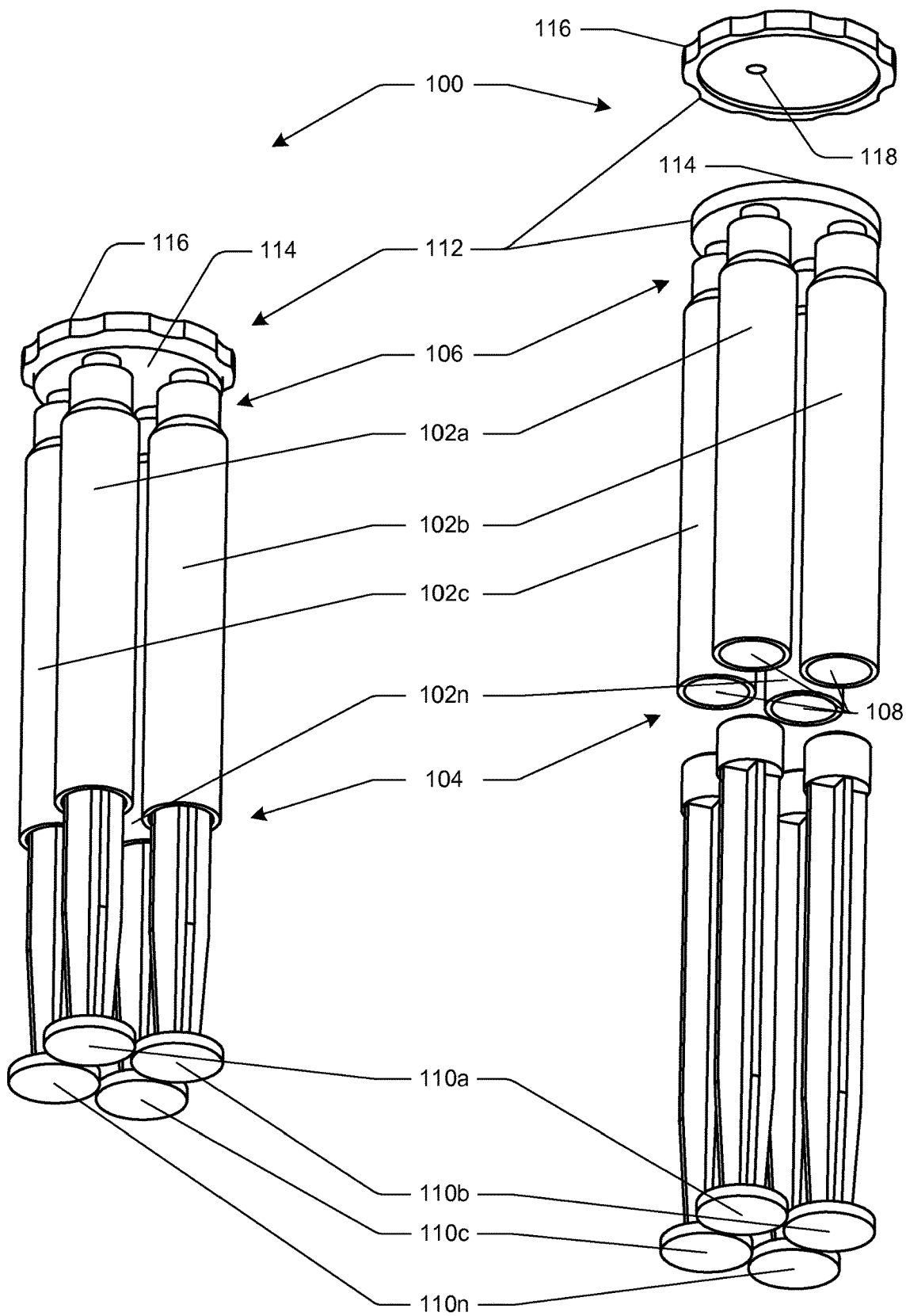
FIG. 1A shows an isometric view of a multi-chambered injection device.
FIG. 1B shows an exploded, isometric view of the multi-chambered injection device of FIG. 1A.

Time is critical for responding to certain medical conditions. For example, a patient suffering from anaphylactic shock may need medicine delivered shortly after the reaction begins. In many instances, particularly for emergent medical conditions, the person administering medicine is not a trained medical professional. Furthermore, even for a trained medical professional, if the necessary medication and equipment are not located in one place it may use valuable time assembling the necessary tools and medicines. Thus, combining multiple medicines in a single device that is easy to use provides significant benefits for treatment of life-threatening medical conditions such as anaphylaxis.

This application describes injection devices that allow a user to administer multiple volumes of the same or different contents. The injection devices may have multiple chambers for holding the contents prior to administering the contents to a patient. The chambers may be the same or similar to a barrel of a syringe. Thus, the chambers may be generally cylindrical and each chamber may be associated with a plunger to expel the contents of the chamber when force is applied to the end of the plunger. The injection devices may have multiple chambers arranged around a central axis in a generally circular pattern. For example, an injection device with three chambers may have the chambers arranged in a triangle. An injection device with four chambers may have the chambers arranged in a square. An injection device with five chambers may have the chambers arranged in a pentagon, and so forth. In other implementations, the chambers may be arranged in a row or even in a different configuration. In an implementation the multiple separate injection devices may be stored in a shared housing. Example injection devices are described generally herein with reference to the accompanying figures.

With reference to FIGS. 1A, 1B, and 2-4, in an example implementation, an injection device 100 has one or more of chambers 102a, 102b, 102c, . . . , 102n with each chamber 102 having a proximal end 104 closer to a user, a distal end 106 closer to a patient, and a chamber cavity 108 that may have contents preloaded therein. The injection device 100 is shown with four chambers 102, but the injection device 100 may have a greater or lesser number of chambers 102. The injection device 100 may be prepared and presented to a user with contents already inside of one or more of the chambers 102. The chambers 102 may be generally cylindrical and each chamber may be associated with a plunger 110a, 110b, 110c, . . . , 110n to expel the contents of the chamber 102 when force is applied to the end of the plunger. The contents may be solids, gases, or fluids. The contents may contain single compounds or compositions of multiple compounds. The contents may be medicine or other non-medicinal contents such as, for example, saline or water. Each of the multiple chambers 102 may contain the same or different contents. In some implementations, two or more chambers 102 may contain the same contents while other chambers 102 contain one or more different contents. Providing the same contents into more chambers 102 provides redundancy and allows the user to "try again" if administration of contents of one chamber 102 failed. For example, this can provide a backup functionality in case there is a failure either with the injection device 100 or with the use of the injection device 100. When one or more of the chambers 102 is preloaded there may also be one or more other chambers 102 that are not preloaded. Empty chambers 102, if present, may remain unused (e.g., the injection device 100 has four chambers 102 but only three are needed for a particular application) or the empty chambers 102 may be filled by the user at or shortly before the time of use.

In one aspect, the injection device 100 may have the chambers 102 preloaded with drugs intended to be used together to treat a specific medical need. For example, treatment of a strong allergic reaction such as anaphylaxis may be addressed by injection of epinephrine (adrenaline), an antihistamine, and if necessary a steroid. A fourth chamber 102 of the injection device 100 may be preloaded with another dose of epinephrine. The antihistamine may be diphenhydramine or a similar antihistamine. The steroid may be a corticosteroid including, but not limited to, cortisone, prednisone, methylprednisolone (Medrol), and dexamethasone (Decadron). In this implementation, each of the drugs in the chambers 102 of the injection device 100 is related to treatment of the same medical condition namely allergic reaction. Equipping one injection device 100 with multiple drugs can provide a range of anti-allergy therapy, i.e., for anaphylaxis, from quick action/short duration, (epinephrine), intermediate action/intermediate duration (antihistamine) to longest onset action/greatest duration of activity (corticosteroid). This configuration places different drugs suitable for treating different aspect of a severe allergic reaction together in a single device. Thus, adrenaline may be administered immediately after the reaction begins, the antihistamine may be administered after the patient initially stabilizes, and the corticosteroid may be administered if there is a prolonged delay receiving professional medical care.

As a further example, the injection device 100 may be used for a patient who is suffering cardiac arrest. Medications loaded into the chambers 102 for treating cardiac arrest may be an anti-arrhythmic (e.g., lidocaine), a vasopressor (e.g., nor-epinephrine), and/or a pH elevator (e.g., sodium bicarbonate). Allergic reactions and cardiac arrest are just two non-limiting examples of medical needs that could be treated with the disclosed multi-chamber injection device 100.

Contents of the chambers 102 may be administered sequentially to a patient. This administration may be in rapid succession, or may be delayed and subsequent drugs may be administered based on response of the patient to the previous administered drug or drugs. Contents of the chambers 102 may be administered intramuscularly or subcutaneously with a needle. Contents of the chambers 102 may be administered through an injection or infusion. Injection into the secretary system of the patient allows the contents, such as medicine, of the chambers 102 to be quickly mobilized to the bloodstream. Contents of the chambers 102 may also be administered intravenously with the needle or with a coupling to a stent. Contents may also be administered intranasally with an appropriate tip joined to the injection device.

Two or more of the chambers 102 may have the same or different volumes. In some implementations the volume of one or more chambers 102 may be about 1 mL. In other implementations the volume of one or more chambers 102 may be about 10 mL. In other implementations the volume of one or more of the chambers 102 may be about 140 mL. According to an embodiment, a volume of one or more chambers may be from about 1 mL to about 140 mL. The volume may be selected based on known volumes of medication suitable for treating a particular medical condition.

Separating the same contents into multiple different chambers 102 may allow for simple adjustment of dosage. That is to say, it may be easier for the user to fully dispense the contents of a first chamber 102 and then, if necessary, use the entire contents of a second chamber 102 rather than partially dispensing the contents of a chamber 102 followed by dispensing the remaining contents of the chamber 102. Because the injection device may have any number of chambers 102, various volumes or dosages may be readily achieved.

Figure 2:
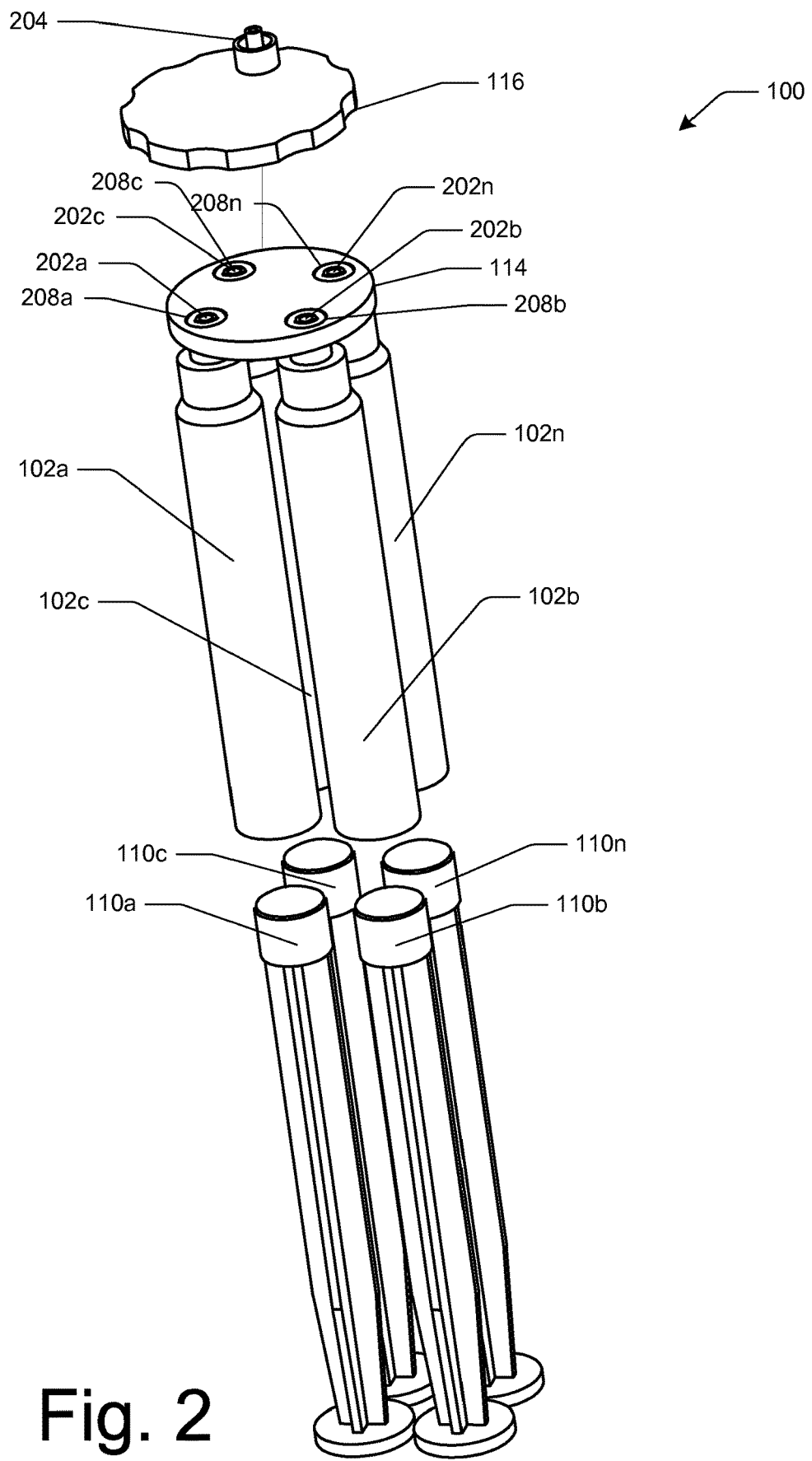
FIG. 2 shows an exploded, isometric view of the multi-chambered injection device of FIG. 1A from a different perspective.
Figure 3:
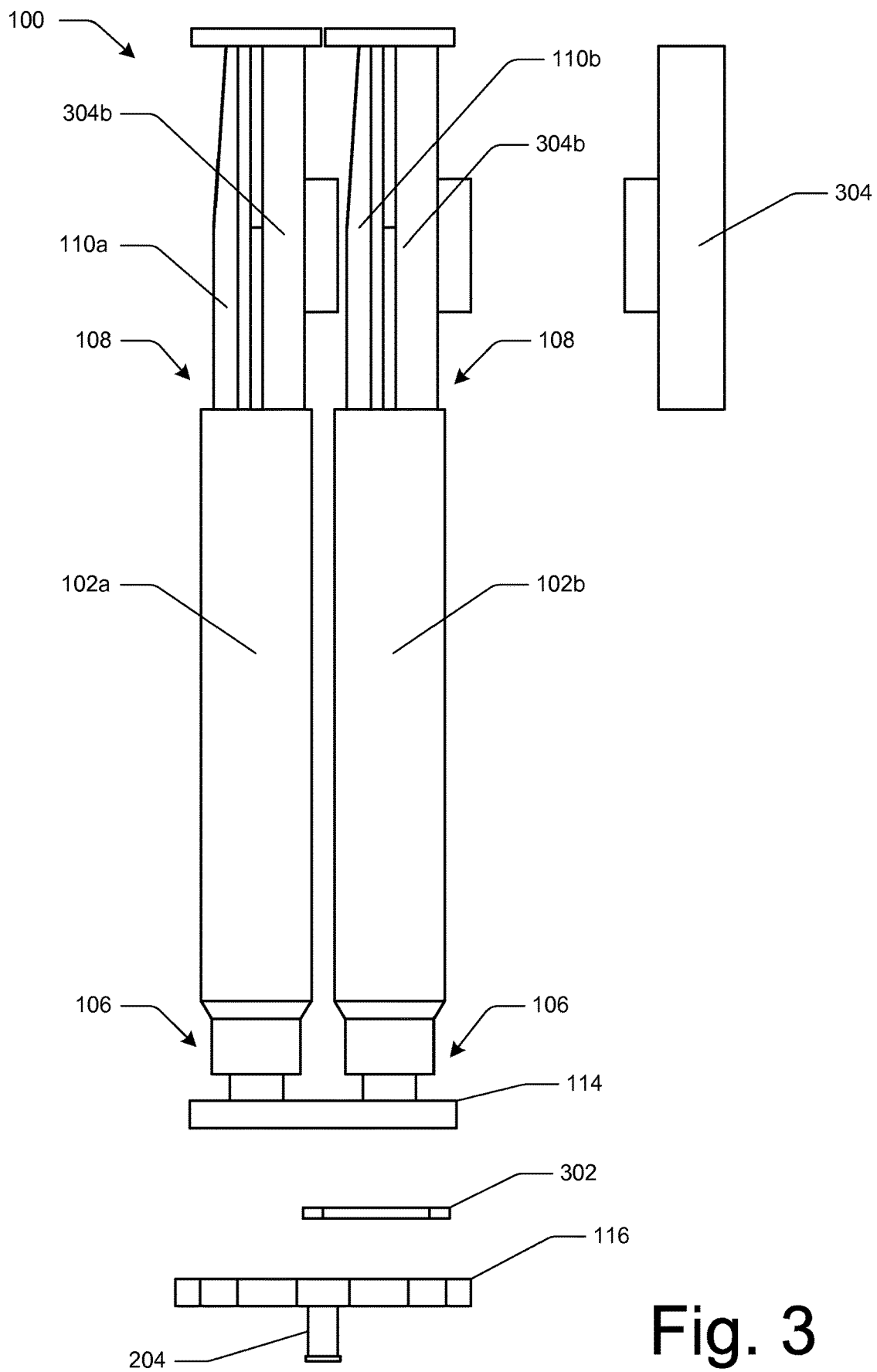
FIG. 3 shows a side view of a multi-chambered injection device with a plunger safety lock.
Figure 4:
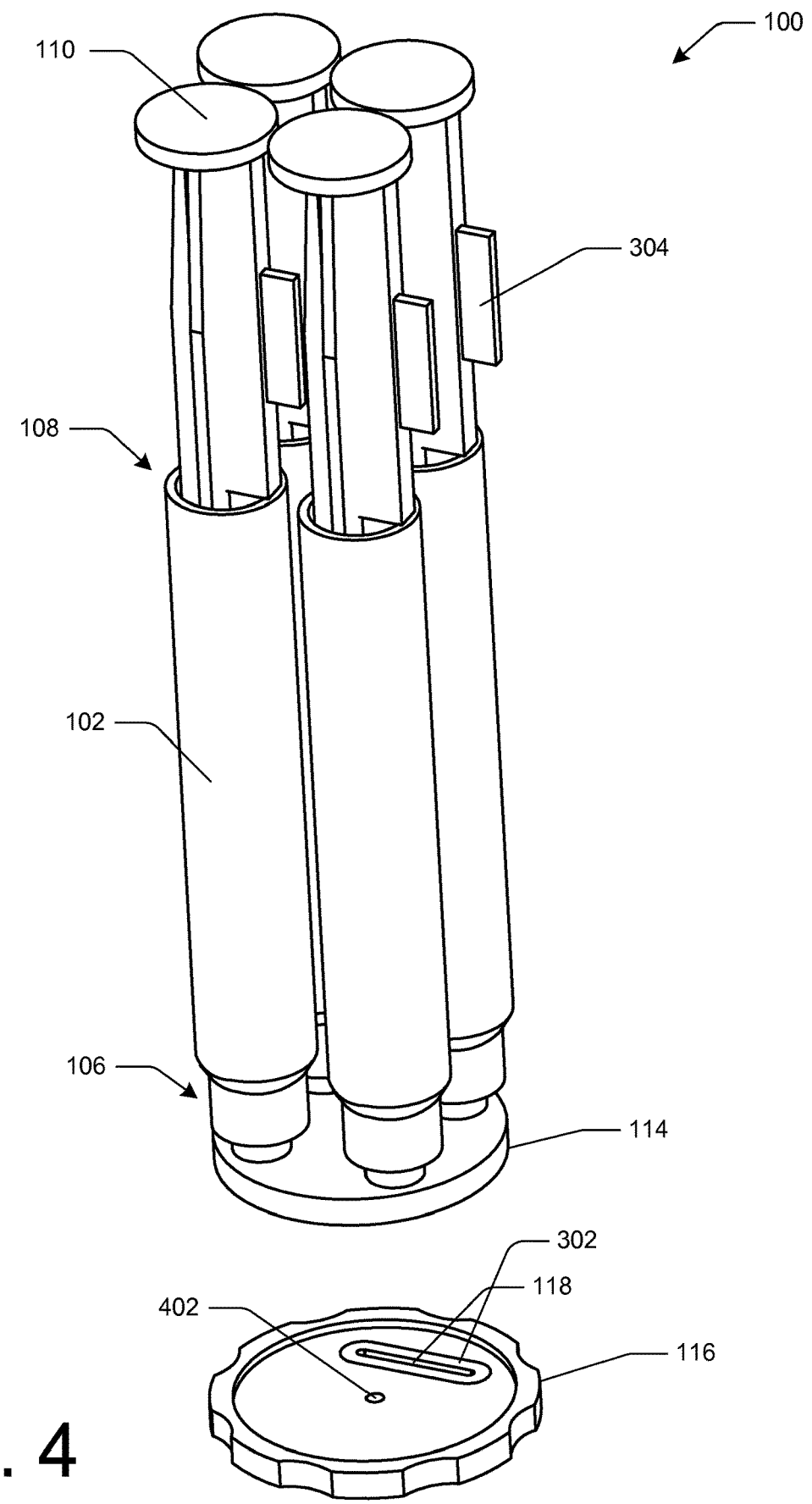
FIG. 4 shows an exploded, isometric view of multi-chambered injection device with plunger safety locks and a slit-shaped outlet.

According to an embodiment, an outlet body 112 is connected to the distal end 106 of the chambers 102. According to an embodiment, the outlet body 112 includes a stationary body 114 that is in direct contact with the chambers 102 and a rotatable body 116 that is moveable connected to or in contact with the stationary body 114. The distal end 106 of each chamber 102 may be coupled to the stationary body 114 via, for example a snap fit or screw fit connection (not shown). In other embodiments, the injection device 100 may be manufactured so that the distal ends 106 of the chambers 102 are fused to the stationary body 114. The distal end 106 of each chamber 102 may be connected to the stationary body 114 such that the distal end 106 of each chamber 102 is in communication with an opening 202a, 202b, 202c, . . . , 202n as shown in FIG. 2. The rotatable body 116 of the outlet body 112 may include one or more outlets 118 which may be aligned with an opening 202 in the stationary body 114 by rotation of the rotatable body 116. According to certain embodiments, the outlet 118 may be in the shape of a circular hole as shown in FIG. 1B or in the form of a slit as shown in FIG. 4. Of course other shapes could be used. According to certain embodiments, each opening 202 may be surrounded by opening seal 208a, 208b, 208c, . . . , 208n to help ensure a tight connection between the opening 202 and outlet 118. In other embodiments, as shown in FIGS. 3 and 4, the outlet 118 may be surrounded by an outlet seal 302 to ensure a tight connection between the opening 202 and outlet 118. The outlet 118 may be a hole that is connected to a hollow needle such as a hyperdermic needle. In some implementations, the outlet 118 may include a connector 204 such as a tapered connector or a locking connector. The connector 204 may form a fluid-tight seal between the chamber 102 and object (such as, for example, a hypodermic needle or tube) coupled to the other end of the connector 204. Examples of such connectors 204 include a Luer tapered connector, a Luer lock connector, and a Luer slip connector. The other end of the connector 204 may be coupled to a needle with a corresponding (e.g., female) connector. Alternatively, the other end of the connector 204 may be coupled to a catheter or stent.

In some implementations, there may be a single outlet 118 shared by the multiple chambers 102. The chambers 102, which may include medication, may communicate or come in contact with outlet 118 by rotating or sliding a portion (e.g., rotatable body 116) of the injection device 100. Rotation may be accomplished by the moving the rotatable body 116 relative to the stationary body 114 located at distal end 106 of the chambers 102. Activation may be performed by a user grasping the injection device 100 in two places and twisting her hands in different directions like wringing out a washcloth. In some implementations, selection of which chamber 102 to discharge the content of may be performed by this simple mechanism that does not require springs or complex and potentially fallible mechanical devices. For example, an injection device 100 with four chambers 102 may be rotated so that a single outlet 118 (or needle—not shown) is aligned with one of the four chambers 102. The other three chambers 102 may be prevented from discharging their contents due to the rotatable body 116 blocking the distal ends 106 of the other chambers 102. Each of the chambers 102 may also be associated with an independent plunger 110. Thus, as a portion of the device is rotated so that the outlet 118 may be aligned with each of the four chambers 102 in turn and the contents of the respective chamber 102 may be dispensed.

The chambers 102 of the injection device 100 may be formed separately and associated with each other through a housing, clip, or other mechanism. Alternatively, multiple chambers 104 may be formed from a single piece of material (e.g., plastic, glass, steel, etc.). Two chambers 102 may be formed as a single piece of material with two cylindrical tubes. Similarly, three chambers 102 may be formed in a generally triangular shaped configuration having three cylindrical tubes within it. As shown in FIG. 1A the chambers 102 may be in a circular configuration. For example, an injection device 100 with six chambers may have the chambers 102 formed from a single piece of material with six cylinders arranged in a circle around a central axis similar in appearance to a cylinder of a revolver.

Clustered chambers 102 may be used with a shared outlet 118 (e.g., a rotatable hole or slot) or with each chamber 102 having its own outlet 118. In configurations in which each chamber 102 has its own outlet 118, attachments to the outlets 118 such as needles may be placed in a configuration to allow easy and interference-free movement.

As shown in FIG. 3, in some embodiments, the injection device 100 may include a plunger safety lock 304a, 304b, . . . and 304n, for each chamber 102 which prevents each plunger 110a, 110b, . . . and 110n from being depressed thus preventing premature expulsion of any contents of the chamber(s) 102. According to an embodiment, the plunger safety lock 304 may be removed by, for example, snap removal.

FIG. 4 shows the outlet 118 formed as a slit. FIG. 4 also provides another view of the plunger safety lock 304 applied to each of the four plungers 110 in this example embodiment. A dimple or hole 402 may be placed at or near the center of the rotatable body 116 to facilitate rotation around a central axis of the injection device 100.

Figure 5:
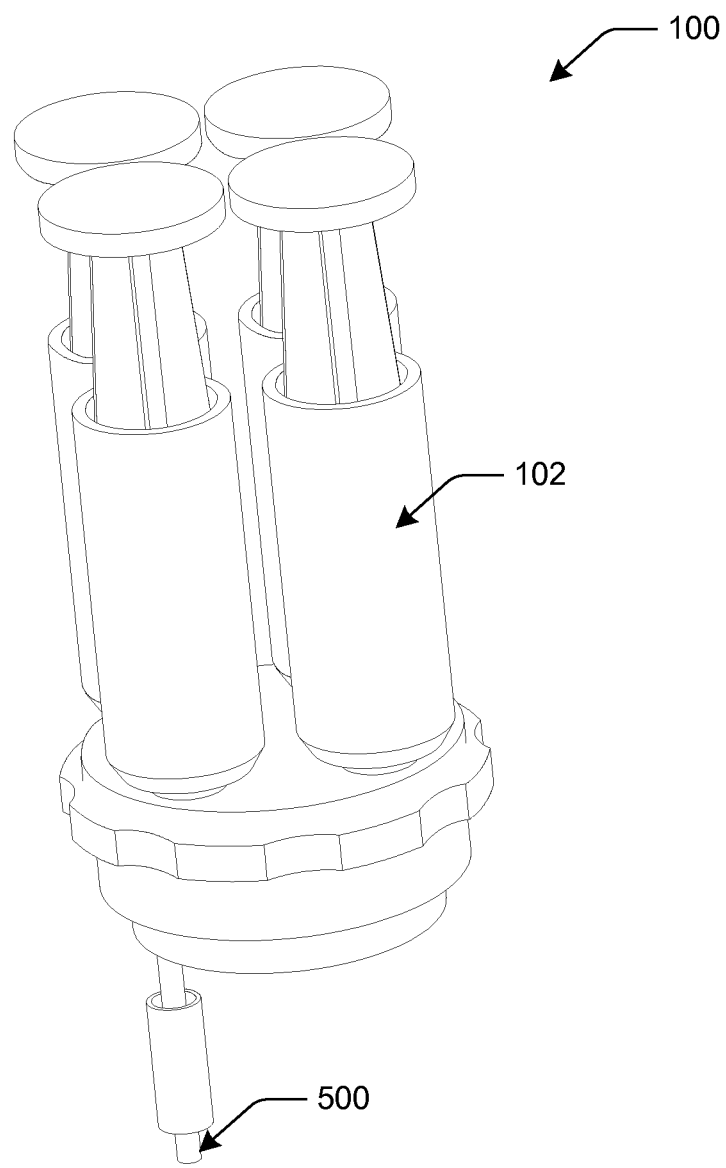
FIG. 5 shows an isometric view of a short multi-chambered injection device.

As shown in FIG. 5, in some implementations the chambers 102 may be shorter with a larger diameter than a standard syringe in order to maintain the same volume of the chambers 102 while shortening the overall length of the injection device 100. This may allow the creation of an injection device 100 that is more compact and portable. Similarly, needles (not shown) on the injection device 100 may also be shorter than standard needles to improve portability. The injection device 100 is shown with a shortened needle 500 coupled to a connector such as the connector 204 shown in FIG. 2. According to an embodiment, the chambers 102 of the injection device 100 may also be formed from a same piece of material. The injection device 100 that allows for delivering multiple injections of potentially different contents with preloaded medicines that are selected to treat a given medical condition is well-suited for field or mobile applications where a large selection of syringes and medication may not be readily available. The injection device 100 may be clearly labeled so that a nonmedical professional is able to easily comprehend the contents of the respective chambers 102 and the appropriate order of administering the contents to a patient.

Returning to the example of treating a patient with a strong allergic reaction, having the necessary medicines for immediate, medium-term, and long-term treatment of the allergic reaction grouped in a single device which also allows for convenient and rapid dispensing of the medications provides a significant benefit over existing devices and techniques for treating strong allergic reactions due to the convenience, ease of use, and simplicity.

Implementations of the injection device 100 that include needles benefit from designs to reduce needle contamination and needle sticks. Coverage of the needle prior to use to prevent contamination and needle sticks may be desirable. Positioning, adjusting orientation, and/or covering of the needle after use to prevent subsequent needle sticks may also be desirable.

Figure 6:
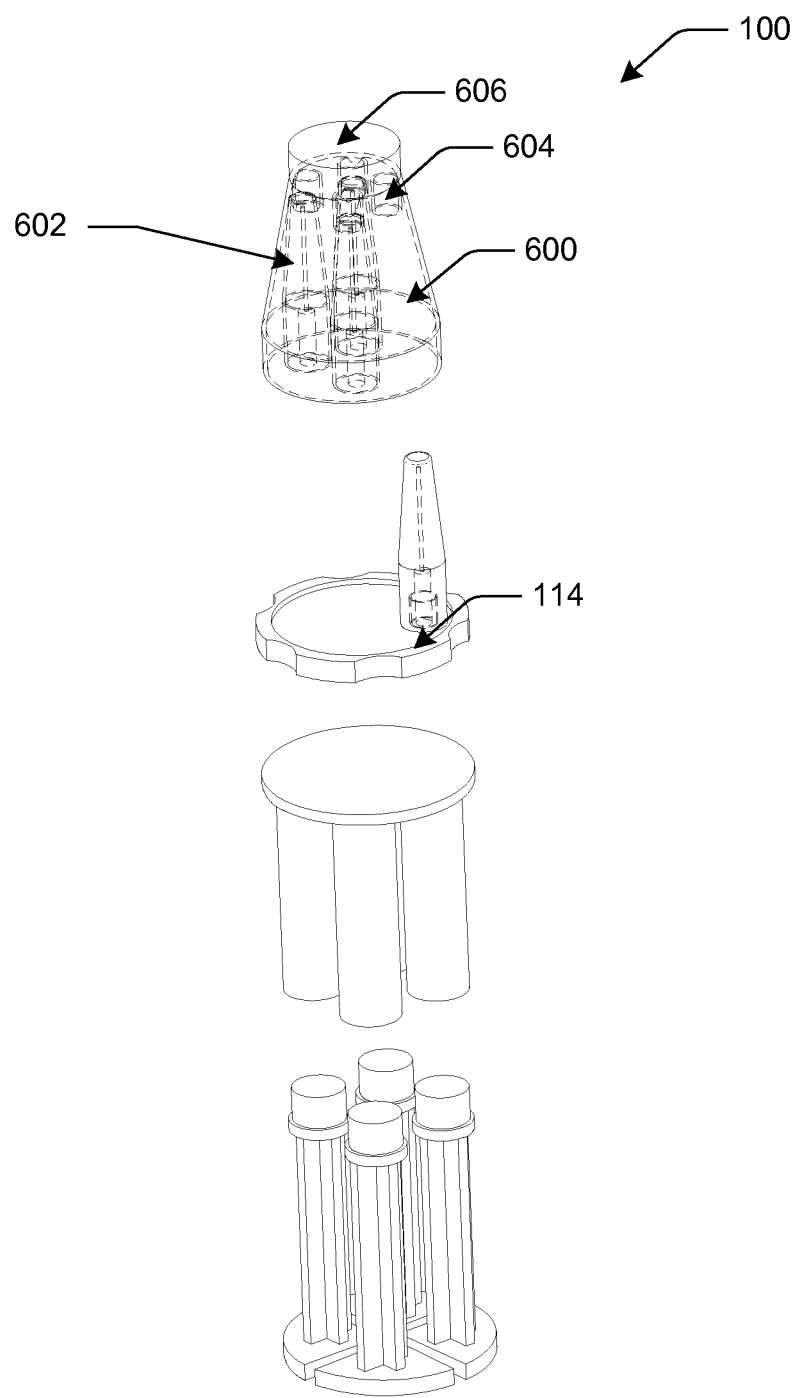
FIG. 6 shows an exploded isometric view of multi-chambered injection devices having a cover.

FIG. 6 shows an embodiment of the injection device 100 that includes a protective cap 600 which may contain one or more spare needles 602 and which covers a needle 602 that is attached to the outlet (not shown), and/or which covers one or more of the openings (not shown) of the chambers 102. A friction-fit, threaded coupling, or other mechanism may be used to couple the protective cap 600 to the injection device 100. In an embodiment, the protective cap 600 may couple to the stationary body 114. The protective cap 600 may contain the same number of needles 602 as the injection device 100 has chambers 102. In an implementation the plurality of needles 602 may be held in the protective cap 600 by insertion of the tips of the needles 602 into a plurality of friction-fit sockets 604 present in an internal surface at a distal portion of the cap 600. Used needles may also be stored by placement into a friction-fit socket 604.

In one implementation the protective cap 600 may contain a sponge 606. The sponge 606 may be sterile and furthermore may also be impregnated with a cleaner. One example of a cleaner is an antiseptic such as alcohol. The sponge 606 may be protected by a sponge cover (not shown). The sponge cover may be made from a single or multilayer foil and/or polymeric laminate. Injection device 100 may be configured with a tear off foil type moisture/vapor barrier covering the sponge 606. The barrier may prevent evaporation of alcohol or other antiseptic, prevent leaking of the disinfectant onto the plungers for other parts of the injection device. Prior to an injection, the user may remove the cover use the sponge 606 and use a disinfectant contained in the sponge 606 to disinfect a skin surface prior to injection. This further increases convenience of the injection device 100 by including an apparatus for disinfecting a skin surface in the same housing as the multi-chamber injection device itself.

The injection device 100 may be used with a variety of methods. For example, when administration of contents of one of the chambers 102 is immediately necessary, the contents may be administered (e.g., by intramuscular injection) without preparing the injection site. If that initial treatment has stabilized the patient, an injection site may be cleansed before subsequent administration of the contents of one of the other chambers 102. The cleansing may be performed by the integrated sponge 606 or with a source of antiseptic or other cleanser that is not necessarily integrated with the injection device 100. Thus, administration of the contents of the first chamber 102 may be done without cleansing the site and then administration of the contents of the second chamber 102 and any additional chambers 102 may be performed after cleansing and/or applying antiseptic to the injection site.

Figure 7:
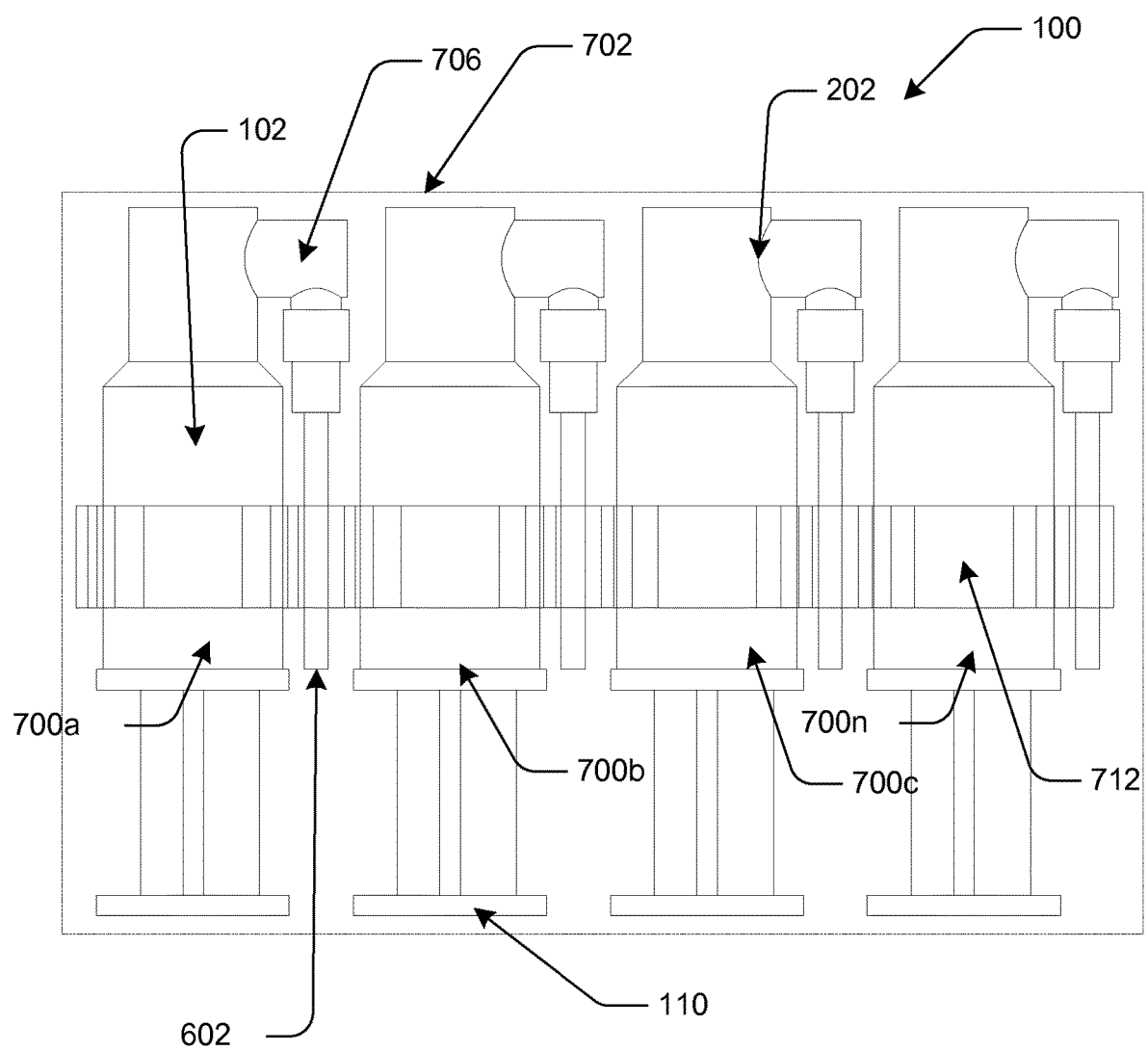
FIG. 7 shows a side view of an embodiment of the injection device in which a plurality of separate syringes are fitted within one container.
Figure 8:
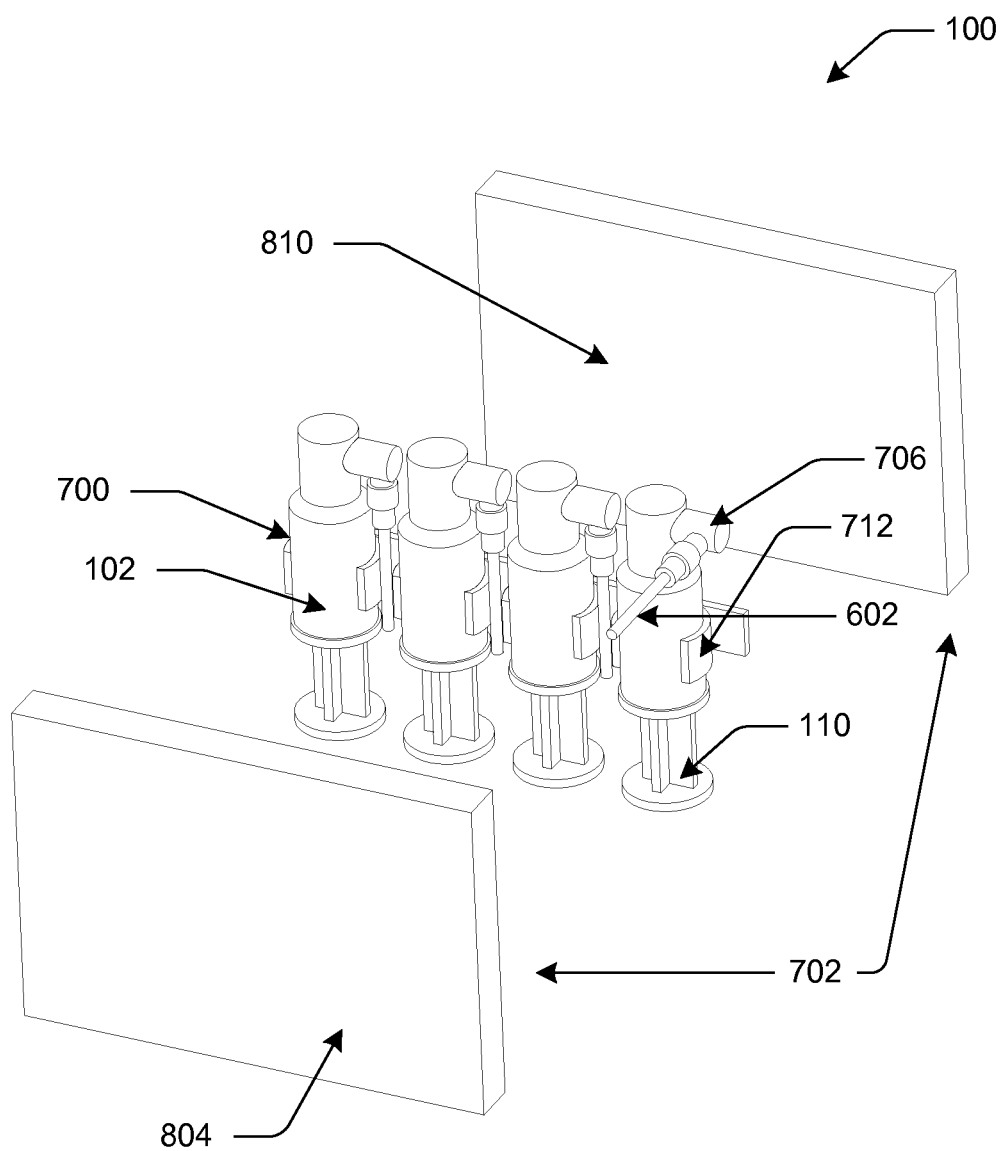
FIG. 8 shows an exploded, isometric view of the injection device of FIG. 7 from a different perspective.

FIGS. 7 and 8 show an embodiment of the injection device 100 in which a plurality of separate syringes 700a, 700b, 700c, . . . , 700n are fitted within one container 702.

Each of the separate syringes 700 may be pre-loaded with contents (e.g., medication, saline, etc.) as described above. Each of the syringes 700 may also be clearly labeled through the use of text, numbers, color or other techniques to indicate to a user the proper order of administration of the pre-loaded contents. For example, the syringes 700 may have different colored plungers 110 that indicate the pre-loaded contents of the respective syringes 700. The container 702 may include additional instructions for use of the syringes 700. Each of the syringes 700 may have a needle 602 attached to the respective chambers 102 of the syringes 700 when the syringes 700 are stored in the container 702. The needle 602 may be in fluid communication with the contents of the chambers 102 or the needle 602 may be attached to the syringe 700 on a pivot 706 that allows the syringe to be rotated alongside the chamber 102. The pivot 706 may break fluid communication between the needle 602 and the syringe 700 when the needle 602 is rotated alongside the chamber 102. In an implementation the needle 602 may be directly connected to an opening 202 on the distal end 106 of the chamber 102 without a pivot 706 (not shown).

The container 702 may fully enclose the syringes 700 and any attached needles 602 in a sterile environment. As shown in FIG. 8, the container 702 may have a lid 804 that is fully removable from a base 810, connected to the base 810 by a hinge (not shown), or connected by any other technique. In some implementations, the edges of the lid and base 810 that mate together may include a seal to maintain sterility inside of the container 702. The container 702 may also include holders 712 that retain the syringes 700 in place within the container 702. The holders 712 may be joined to or a part of the base 710. In an implementation, the holders 712 may keep the syringes 700 mounted within the container with the long dimension of the syringes 700 parallel to each other. In other implementations the plurality of syringes 700 may be mounted linearly or circularly in the container 702 by the holders 712.

CONCLUSION

Although the application describes implementations having specific structural features, compounds/compositions, and/or methodological acts, it is to be understood that the claims are not necessarily limited to the specific features or acts described. Rather, the specific features and acts are merely illustrative some implementations that fall within the scope of the claims of the application.

What is claimed is:

1. A multi-chamber syringe comprising:
   three or more chambers arranged parallel to each other and parallel to a central axis;
   a plunger associated with each of the three or more chambers; and
   an outlet body rotatably connected to the three or more chambers such that at least a portion of the outlet body rotates around the central axis positioning an outlet in fluid communication with one of the three or more chambers while blocking release of fluid from the other chambers;
   wherein two or more of the chambers contain different drugs both usable to treat a same medical condition,
   wherein the multi-chamber syringe further comprises a cap removably covering the outlet, wherein the cap comprises storage for a plurality of needles, wherein the storage for the plurality of needles comprises a plurality of friction-fit sockets present in an internal surface at a distal portion of the cap, and wherein each of the plurality of needles is stored parallel to the central axis in one of the plurality of friction-fit sockets.

2. The multi-chamber syringe of claim 1, further comprising a fourth chamber arranged parallel to the other three or more chambers and parallel to the central axis, wherein the fourth chamber contains epinephrine.

3. The multi-chamber syringe of claim 1, wherein the three or more chambers are formed from a single piece of material.

4. The multi-chamber syringe of claim 1, wherein a volume of one or more of the three or more chambers is from 1 mL to 140 mL.

5. The multi-chamber syringe of claim 1, wherein the three or more chambers are formed separately and associated with each other through attachment to the outlet body.

6. The multi-chamber syringe of claim 1, wherein the outlet body has only a single outlet.

7. The multi-chamber syringe of claim 1, wherein the outlet body has a first portion fixedly attached to the three or more chambers and a second portion rotatable coupled to the first portion and configured to rotate relative to the first portion around the central axis.

8. The multi-chamber syringe of claim 1, wherein the outlet comprises a hollow needle.

9. The multi-chamber syringe of claim 1, wherein the outlet comprises a Luer connector.

10. The multi-chamber syringe of claim 1, wherein the same medical condition is an allergic reaction and a first chamber of the three or more chambers contains epinephrine, a second chamber of the three or more chambers contains an antihistamine, and a third chamber of the three or more chambers contains a corticosteroid.

11. The multi-chamber syringe of claim 1, wherein the same medical condition is a heart attack and a first chamber of the three or more chambers contains an anti-arrhythmic, a second chamber of the three or more chambers contains a vasopressor, and a third chamber of the three or more chambers contains a pH elevator.

12. The multi-chamber syringe of claim 1, further comprising a plunger lock to prevent accidental operation of at least one of the plungers.

\* \* \* \* \*